(12) United States Patent
Spong et al.

(10) Patent No.: US 9,410,919 B2
(45) Date of Patent: Aug. 9, 2016

(54) ELECTROCHEMICAL GAS DETECTOR WITH CARBON ELEMENT

(71) Applicant: LIFE SAFETY DISTRIBUTION AG, Uster (CH)

(72) Inventors: Alan Daniel Spong, Hedge End (GB); John Chapples, Portsmouth (GB); Neils Richard Stewart Hansen, Poole (GB)

(73) Assignee: Honeywell International Inc., Morris Plains, NJ (US)

( * ) Notice: Subject to any disclaimer, the term of this patent is extended or adjusted under 35 U.S.C. 154(b) by 528 days.

(21) Appl. No.: 13/901,090

(22) Filed: May 23, 2013

(65) Prior Publication Data
US 2013/0319858 A1   Dec. 5, 2013

Related U.S. Application Data

(60) Provisional application No. 61/653,508, filed on May 31, 2012.

(51) Int. Cl.
*G01N 27/403* (2006.01)
*G01N 27/404* (2006.01)

(52) U.S. Cl.
CPC .......... *G01N 27/403* (2013.01); *G01N 27/404* (2013.01)

(58) Field of Classification Search
CPC .................... G01N 27/403; G01N 27/404
USPC ................................................ 204/430–432
See application file for complete search history.

(56) References Cited

U.S. PATENT DOCUMENTS

| | | | | |
|---|---|---|---|---|
| 4,988,582 A | * | 1/1991 | Dyer | H01M 8/1002 29/623.5 |
| 7,931,788 B1 | * | 4/2011 | Wilkins | G01N 33/5438 204/403.01 |
| 2002/0125131 A1 | * | 9/2002 | Babes-Dornea | G01N 27/4045 204/415 |
| 2003/0087156 A1 | * | 5/2003 | Broman | H01M 4/8615 429/235 |
| 2003/0209442 A1 | * | 11/2003 | Harper | G01N 27/4045 205/108 |
| 2008/0096075 A1 | * | 4/2008 | Lundblad | C25B 9/10 429/492 |

OTHER PUBLICATIONS

Lux et al. (J. Electrochem. Soc, 159/11, A1849-A1855, published Sep. 11, 2012).*

* cited by examiner

*Primary Examiner* — Luan Van
*Assistant Examiner* — Steven Rosenwald
(74) *Attorney, Agent, or Firm* — Conley Rose, P.C.; Kristin Jordan Harkins

(57) ABSTRACT

An electrochemical detector includes a carbon based element located between a separator and a current collector of an adjacent electrode. Elements can take the form of a carbon fabric located between the separator and the collector, or a linear, or, circular carbon deposit on a surface of the separator adjacent to the respective current collector. Other conductive coatings including gold, platinum or transition metals, as well as carbon, can be deposited directly onto a porous substrate, such as a masked separator material.

15 Claims, 2 Drawing Sheets

ELECTROCHEMICAL GAS DETECTOR WITH CARBON ELEMENT

CROSS-REFERENCE TO RELATED APPLICATION

This application claims the benefit of the filing date of U.S. Provisional Application Ser. No. 61/653,508 filed May 31, 2012, entitled, "Electrochemical Sensor with Contact Disk". The '508 application is hereby incorporated herein by reference.

FIELD

The application pertains to electrochemical gas detectors. More particularly, the application pertains to such detectors which include a carbon element to provide improved contact between a current collector and an adjacent electrode.

BACKGROUND

Under some circumstances, a loss of contact can occur between platinum wire current collectors, and adjacent electrodes (sensing, reference or counter electrodes) in an electrochemical detector. Some detectors, when thermally cycled, can exhibit that loss of contact between the electrode and wire current collector that result in loss of sensor output. This occurs because the current collector wire can become and remain embedded in adjacent, compressible separator material, which can move away from the comparatively non-deformable electrode. Other environmental changes such as operation in dry atmospheres resulting in drying out of separators and thermal cycling of sensors can also be responsible for unfavorable contact issues. It would be desirable to provide a generic method to improve the reliability of electrode contacts at all electrodes in the sensor.

DETAILED DESCRIPTION

Figure 1:
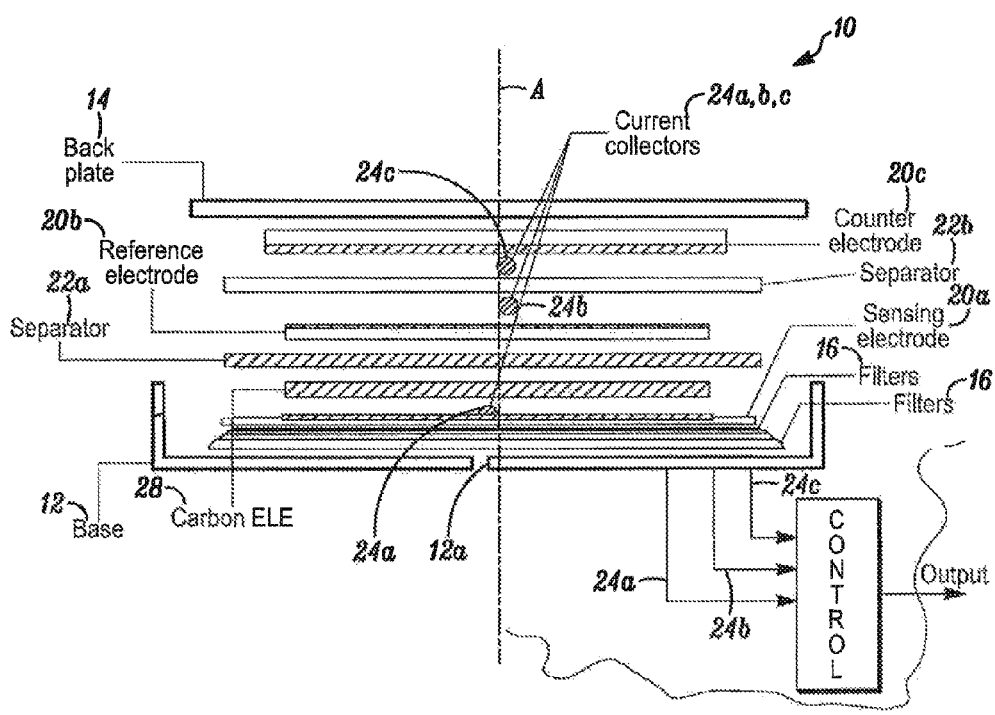
FIG. 1 is an exploded, sectional view of a detector in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

When the sensor is thermally cycled the compression between the components can be affected. When this occurs a current collector can become and remain imbedded in a separator as it moves away from the conductive electrode.

FIG. 1 illustrates an electrochemical gas detector 10 in accordance herewith. A cylindrical base 12 has a closing, circular or disk shaped back-plate 14. It will be understood that neither the exact shape, nor the exact configuration of the detector 10, except to the extent described below, are limitations hereof. A gas access port 12a is centrally located in base 12 with filters 16 carried adjacent thereto in the base 12.

Electrodes 20a, b, c are located in base 12 and extend axially along a common center line A. Non-conductive separators 22a, b are located adjacent to respective electrode pairs such as 20a and 20b or 20b and 20c. Current collectors 24a, b, c extend between respective electrode-separator pairs, such as 20a, 22a 20b, 22b and 20c and 22b. As those of skill will understand, where the base and back-plate 12, 14 are cylindrical, the electrodes and separators could also be cylindrical or disk shaped. Other geometries could be used as required for a given sensor form factor.

As will also be understood, the separator elements, in an assembled detector, such as detector 10, force the collectors, such as 24a, b, c into continual and reliable contact with respective electrodes, such as 20a, b, c.

To improve this coupling between the collectors and the electrodes, where the collectors might become embedded in the respective adjacent separator element, additional conductive paths between collectors and electrodes can be provided. Either carbon cloth or deposited carbon conductive elements can be used, as explained below.

FIG. 1 illustrates one possible placement of a carbon element 28 (implemented as a separate disk 30, or a deposit 30 a, or b) in the detector 10. Preferably, where element 28 is implemented as in FIG. 2, the disk 30 is placed between the sensing electrode current collector 24a and the separator 22a as shown in FIG. 1. Similar components may also be used in conjunction with the other electrodes. For example, a disk such as 30 can be located adjacent to separator 22b and collector 24b, or separator 22b and collector 24c.

Figure 2:
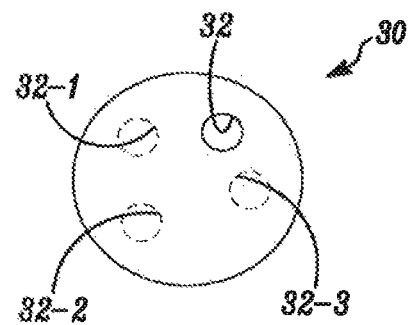
FIG. 2 is a planar view of a carbon cloth disk for use in the detector of FIG. 1.

The disk 30, see FIG. 2, can be formed by punching for example, a carbon cloth-type material. Exemplary thicknesses are in a range of 100-200 micrometers.

It will be understood by those of skill in the art that additional wicking can be provided by punching a hole, such as hole 32, in the carbon cloth disk 30. In this regard, FIG. 2 illustrates a carbon cloth disk 30 which has a punched hole 32 to provide added wicking. In instances where detector volume is relatively low, it is particularly desirable to ensure that electrolyte is effectively transported around the cell. One or more punched holes 32-1, -2 or -3 can be provided in various locations in disk 30. A single opening can be centrally located, and when the detector is assembled, that opening can be expected to be centered on the axis A.

The above-described contact aid may also be used in conjunction with other forms of cells. These include, for example those using gel or polymer electrolytes rather than liquid-soaked separators. These can also suffer from issues of contact loss due to the compliant nature of some of the materials.

By placing the cloth disk 30 between the separator 22a and the adjacent current collector 24a the current collector can be kept from imbedding into the non-conductive material of the separator 22a. Further, if the wire current collector, such as 24a, loses contact with the sensing electrode 20a, it will maintain contact with the punched cloth disk 30 which in turn will remain in contact with the electrode 20a.

Although the example given here uses a carbon cloth disc, it will be understood that other materials may be able to fulfill the same function. Ionic conductive characteristics for electrolytic conductivity through the cell results from wetting by the surrounding electrolyte. The electronic conductivity for current collection is exhibited by conductive materials. The material should be chemically and electrochemically stable in the electrolyte environment of the sensor (typically strong acid or strong alkali). The material needs to have an appropriate degree of resistance to compression, and be mechanically stable across the full operating temperature range. It must be stable in both low and high humidity conditions and preferably does not demonstrate any electrochemical activity within the operating voltage window of the cell. Finally, all of these properties must be maintained throughout the life of the sensor.

Figure 3:
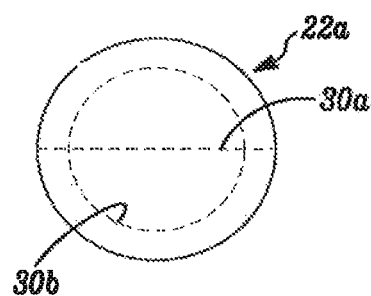
FIG. 3 illustrates a plain view of alternate carbon elements.

Alternatively, with respect to FIG. 3, "carbon-based" formulations can be deposited/printed onto a separator material to produce a line, such as 30a, or curve, "pad" 30b, or other-shaped conductive feature of deposited conductive material beneath a current collector, such as 24a, pressed against an electrode surface, such as 20a, to ensure a maximum contact resistance between the current collector and electrode of on the order of 30 ohms, independent of the extent of local "separation" between the components that may have resulted from densification of the separator from localized mechanical compression, either from thermal cycling, mechanical shock etc. The line 30a or curve element 30b can be formed of continuous or intermitted deposits on the non-conductive separator material. For example, intermittent pads of 2.5 mm can be deposited to form a more extensive conductive feature. It should be noted that the formulation will occur on the surface of the material but some will also penetrate into the material.

The carbon-based formulation contains one or more forms of carbon. Standard methods can be used to deposit the formulation, i.e. spraying, stencil/directly printing.

Technical graphite can be used as a carbon source. A relative pure graphite based solution is another possible alternate. A mixture of these two graphites is also contemplated.

A finely divided form of silica (Silica, fumed powder, 0.007 μm Sigma Aldrich part no. S5130-100G) can be incorporated into the carbon-based formulation at 3-15% w/w. The silica is inert but has a higher surface energy than the graphite-based materials alone. Other publicly available, similar acid resistant materials which can impart similar improvements to the wettability of the structure come within the spirit and scope hereof.

A noble metal coated carbon or "graphite supported catalyst" (specifically 5% w/w platinum supported on the same technical graphite, supplied by Johnson Matthey) can be used as a carbon source or in addition to the carbon sources above to increase the surface energy. Other variations are possible as would be understood by those of skill in the art.

The formulations can also contain an amount of polymer sufficient to "bind" the conductive powder particles together and to the separator material. The polymer must be tolerant of the strong sulfuric acid electrolyte used for oxygen pump detectors.

An exemplary polymer is polytetrafluoroethylene (PTFE). To maximize the "wettability" of the contact aid, a small amount of PTFE can be added to the carbon formulation (as it lowers the surface energy of the deposit appreciably) but sufficient to create mechanical strength (5-20% w/w PTFE in the formed deposit is the recommended amount.

Carbon-based formulation deposits, as noted above, can extend continuously or intermittently and can be on top of the surface and within the middle of the material.

An alternative polymer that may be added to the carbon-based formulation is an ionically conductive polymer, such as that commercially available under the Nafion™ brand. In addition, the ionically conductive polymer can be deposited on the material in the absence of carbon.

As a further example, formulations to produce acceptable deposits contain the following components and compositions in the final deposited structure as follows:
Nafion brand polymer (50-75% w/w)
5% w/w platinum supported on technical graphite (20-40% w/w)
Fumed silica (3-15% w/w)

Two additional examples, A and B Catalyst Content (% w/w)

| Component | A | B |
|---|---|---|
| 5% Pt on graphite | 30 | 26 |
| Nafion | 70 | 67 |
| Fumed silica | 0 | 7 |

In addition, the deposition of conductive coatings using sputter coating techniques would achieve similar results. Use of conducting coatings such as gold, platinum and other transition metals and carbon directly onto a porous substrate such as a masked separator material.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be added to or removed from the described embodiments.

The invention claimed is:

1. An electrochemical gas detector comprising:
   at least one sensing electrode with an adjacent non-conducting separator; and
   a conductive element located between and in contact with each of the non-conducting separator and the sensing electrode, wherein the conductive element comprises a plurality of intermittent carbon-based formulation deposits deposited on the separator, and wherein the plurality of intermittent carbon-based formulation deposits comprises spaced apart cylindrical members having a diameter on the order of 2.5 mm.

2. An electrochemical gas detector as in claim 1, further comprising: a metal current collector located between the conductive element and the electrode.

3. An electrochemical gas detector as in claim 1, further comprising: control circuits coupled to the at least one sensing electrode, and, a housing, wherein the housing contains the at least one sensing electrode, the non-conducting separator, and the conductive element, wherein a gas access port in the housing is positioned adjacent to a filter.

4. An electrochemical gas detector as in claim 1, wherein the plurality of intermittent carbon-based formulation deposits comprises carbon selected from the group consisting of technical graphite, pure graphite and mixtures thereof.

5. An electrochemical gas detector as in claim 1, wherein the plurality of intermittent carbon-based formulation deposits further comprises fumed silica.

6. An electrochemical gas detector as in claim 1, wherein the plurality of carbon-based formulation deposits further comprises a noble metal coated carbon.

7. An electrochemical gas detector comprising:
   a housing, the housing carries at least one electrode adjacent to a non-conducting separator; and
   a conductive element located between and in contact with each of the non-conducting separator and the sensing electrode, wherein the conductive element comprises a plurality of intermittent carbon-based formulation deposits deposited on the separator, and wherein the plurality of intermittent carbon-based formulation deposits comprises spaced apart cylindrical members having a diameter on the order of 2.5 mm.

8. An electrochemical gas detector as in claim 7, wherein the separator has first and second spaced apart surfaces, and where the at least one electrode is adjacent to one surface and the conductive element is adjacent to the at least one electrode with a collector extending between the conductive element and the at least one electrode.

9. An electrochemical gas detector as in claim 8, further comprising a second electrode adjacent to the second surface of the separator.

10. An electrochemical gas detector as in claim 7, wherein the conductive material is deposited by one of spraying, stenciling, or printing.

11. An electrochemical gas detector as in claim 7, wherein the conductive element is one of circular or linear conductive deposit comprising the plurality of intermittent carbon-based formulation deposits deposited on the separator.

12. An electrochemical gas detector as in claim 9, wherein the plurality of carbon-based formulation deposits comprises carbon selected from the group consisting of technical graphite, pure graphite, and mixtures thereof.

13. An electrochemical gas detector as in claim 7, wherein the plurality of intermittent carbon based formulation deposits further comprises fumed silica.

14. An electrochemical gas detector as in claim 7, wherein the plurality of intermittent carbon-based formulation deposits further comprises a noble metal coated carbon.

15. An electrochemical gas detector comprising:
a conductive element located between a non-conducting separator and a current collector of an adjacent electrode, wherein the conductive element comprises a linear or circular conductive deposit on the non-conducting separator adjacent to the respective current collector, wherein the linear or circular conductive deposit comprises a plurality of intermittent carbon-based formulation deposits deposited on the separator, and wherein the plurality of intermittent carbon-based formulation deposits comprises spaced apart cylindrical members having a diameter on the order of 2.5 mm.

\* \* \* \* \*